US006436716B1

(12) United States Patent
Wu

(10) Patent No.: US 6,436,716 B1
(45) Date of Patent: Aug. 20, 2002

(54) ALDEHYDE TEST STRIP

(75) Inventor: Wen H. Wu, Elkhart, IN (US)

(73) Assignee: Integrated Biomedical Technology, Inc., Elkhart, IN (US)

( * ) Notice: Subject to any disclaimer, the term of this patent is extended or adjusted under 35 U.S.C. 154(b) by 47 days.

(21) Appl. No.: 09/583,050

(22) Filed: May 30, 2000

(51) Int. Cl.$^7$ ............................................. G01N 31/22
(52) U.S. Cl. ...................... 436/128; 436/130; 436/169; 422/55; 422/56; 422/57
(58) Field of Search ................................ 436/128, 130, 436/169; 422/55, 56, 57

(56) References Cited

U.S. PATENT DOCUMENTS

| | | | | |
|---|---|---|---|---|
| 4,298,569 A | * | 11/1981 | Read | 422/27 |
| 4,328,182 A | | 5/1982 | Blake | 422/56 |
| 4,438,206 A | * | 3/1984 | Nakajima et al. | 436/130 |
| 4,521,376 A | | 6/1985 | Witonsky et al. | 422/56 |
| 4,643,980 A | | 2/1987 | Witonsky et al. | 436/128 |
| 5,112,741 A | * | 5/1992 | Palmer et al. | 435/25 |
| 5,464,775 A | * | 11/1995 | Smith | 436/63 |
| 6,063,631 A | * | 5/2000 | Ignacio | 436/1 |

FOREIGN PATENT DOCUMENTS

| | | | |
|---|---|---|---|
| WO | 97/33978 | * | 9/1997 |

OTHER PUBLICATIONS

J. Frederic Walker, *Formaldehyde*, 3rd ed., Reinhold Publishing Corporation, NY, NY (1964), Chapters 14 (pp. 359–414), 17 (pp. 467–482), and 18 (pp. 483–510).
Brochure, Reuse of hemodialyzers, *Association for the Advancement of Medical Instrumentation*, ANSI/AAMI RD47, pp.1–26 1993.
Brochure, Hemodialyzer reuse: Issues and solutions, *AAMI Analysis and Review*, TAR No. 10–85, pp. 135–139, 141–143, 145–153 (1985).
Lynch, Evaluation of the efficacy and safety of sporicidin–HD and formaldehyde in reprocessed dialyzers: a comparative study, *Hemodialyzer Reuse: Issues and Solutions*, pp.154–159, 1985.
Wendt et al., Safety, efficacy and performance of CIDEX dialyzer disinfectant for reprocessing hemodialyzers, *Hemodialyzer Reuse: Issues and Solutions*, pp. 160–165, 1985.
Product Brochure, *Ultrafast* Nephretect, Formaldehyde & Glutaradelhyde Test Reagent, (Oct. 16. 1996).
Product insert, Serim Formaldehyde Test Strips (Feb., 1998).
Product insert, Maxi–Strip, Dialdehyde Concentration Indicator (Undated).
Product insert, Cidexplus (Undated).
Product insert, CIDEX* Family of Solutions Test Strips (1994).
Product insert, Serim Disintek XL Test Strips (Jun. 2000).
Serim Research Corp., website (Sep. 14, 2000—printed).
Product insert, MaxiCide (Undated).
Product insert, MaxiCide Plus (Undated).
Material safety data sheet, label, and product insert WAVICIDE–01 (1998).
Product insert and copy of container, Cidexplus (Undated).
Product insert and copy of container, Cidex (Undated).
"Safe use and handling of glutaraldehyde–based products in health care facilities," American National Standard, ANSI/AAMI ST58 (1996).
Product insert, Omnicide® 28 (Undated).

* cited by examiner

*Primary Examiner*—Jill Warden
*Assistant Examiner*—LaToya Cross
(74) *Attorney, Agent, or Firm*—Marshall, Gerstein & Borun

(57) ABSTRACT

A composition, method, and device for quantitatively determining the concentration of an aldehyde in a sample are disclosed. The device includes a test pad having a suitable carrier matrix incorporating an indicator reagent composition capable of interacting with the aldehyde to produce a detectable and measurable response for aldehyde concentration over a range of 0% to over 4%, by weight of the sample. An indicator reagent composition contains: (a) a protein, (b) an amine, (c) a color indicator, (d) preferably a neutral, nonionic polymer, such as a water-soluble cellulose polymer, and (e) a carrier. An indicator reagent composition is incorporated into a carrier matrix, like filter paper, to provide a test pad useful in a dry phase aldehyde assay of a sample, especially for samples containing a high concentration of glutaraldehyde or formaldehyde.

36 Claims, No Drawings

ALDEHYDE TEST STRIP

FIELD OF THE INVENTION

The present invention relates to a composition, method, and device for determining the concentration of an aldehyde in a sample. More particularly, the present invention relates to a method and device for assaying an aqueous sample for an aldehyde concentration over the range of 0% to greater than 4%, by weight, by using an improved indicator reagent composition. Contrary to prior compositions, the present indicator reagent compositions have the advantage of quantitatively measuring a high range of aldehyde concentration in a sample without requiring multistep titration procedures. The invention is particularly effective for determining the concentration of a monoaldehyde, such as formaldehyde, or a dialdehyde, such as glutaraldehyde.

BACKGROUND OF THE INVENTION

Aldehydes have been used for many years in the medical sciences for various purposes. It is well known, for example, that formaldehyde and glutaraldehyde are useful for fixing and preserving tissue specimens. In recent years, the role of aldehydes in the medical community has expanded to that of a germicide useful for disinfecting or sterilizing medical instruments.

The use of formaldehyde and glutaraldehyde in disinfecting and sterilizing hemodialyzers is particularly common. Due to the proliferating reuse of hemodialyzers, the need for safe, accurate, and efficient methods of testing for disinfectant levels in the eluant of a hemodialyzer has increased dramatically.

The effectiveness of the germicidal solution depends on the concentration of the aldehyde. Currently, 2% glutaraldehyde and 4% formaldehyde, by weight, are used as germicidal solutions. These germicidal solutions are commercially available or can be manually prepared. The monitoring of the aldehyde levels in the solution is particularly important in assuring the effectiveness of the disinfectant. Unfortunately, the procedures presently available generally either require a multistep titration, lack accurate quantification, or involve complicated sample preparation, which hampers the convenience and efficiency of the assay.

For instance, several colormetric procedures are available for the detection of trace amounts of formaldehyde. The test kits for these colormetric assays, however, are only available in an ampule format. The procedures commonly employ Schiff's reagent or Edgriwe's reagent as the indicator. Schiff's reagent, which is prepared from rosaniline and bisulfite in concentrated hydrochloric acid, and Edgriwe's reagent, which consists of chromotropic acid in strong sulfuric acid, both require strong acid. However, strong acids generally are avoided in a dry reagent strip test because the corrosive nature of the acids degrades the carrier, typically cellulose, for the indicator reagent composition.

In addition, in some cases, the colormetric procedures require heat for the reaction to occur, which also is inconsistent with a convenient, quantitative dry reagent strip test. Moreover, the detection ranges of current colormetric procedures are extremely sensitive, i.e., detect formaldehyde concentrations in the range of parts per million (ppm), and are not suitable for the measurement of higher aldehyde concentrations in the weight percent (%) ranges.

For the determination of percent levels of formaldehyde, the sodium sulfite and sodium bisulfite methods have been used. In these methods, the reaction of a sodium sulfite or sodium bisulfite reagent with formaldehyde generates an equal molar amount of sodium hydroxide. The amount of formaldehyde is estimated from the amount of acid required to titrate the generated sodium hydroxide. For a more thorough description of the sodium sulfite and sodium bisulfite methods, see J. F. Walker, "Quantitative Analysis of Formaldehyde," in *Formaldehyde*, 3rd ed., Reinhold Publishing Corporation, New York, N.Y., pp. 486-488 (1964). Though accurate, each method requires multiple steps leading up to the titration. In addition, the production of caustic sodium hydroxide makes it difficult to provide a quantitative dry reagent strip assay.

Organic nitrogen compounds, such as amines, amides, ureides, amino acids, and proteins having a hydrogen bonded to the nitrogen, also react with formaldehyde to provide a useful assay for formaldehyde content. For example, formaldehyde reacts with lower amino acids, such as alanine, asparagine, and glycine in an aqueous solution. The aqueous solutions of these lower amino acids have a slightly acidic or neutral pH. In the presence of formaldehyde, however, the amino acids react as strong acids. The concentration of formaldehyde can be determined by end point titration of the amino acid-formaldehyde solution with an alkaline solution. Further description of the reaction of formaldehyde with organic nitrogen containing compounds, and more particularly amino acids, can be found in J. F. Walker, "Reaction with Amines, Amides and Nitriles," in *Formaldehyde*, 3rd ed., Reinhold Publishing Corporation, New York, N.Y., pp. 359-414, in particular pp. 395-398 (1964).

The reaction of another aldehyde, glutaraldehyde, with a mixture of sodium sulfite and an amine compound, for example glycine, is the subject of various U.S. patents. U.S. Pat. Nos. 4,521,376 and 4,463,980 describe a test system for glutaraldehyde consisting of a mixture having a defined ratio of sodium sulfite and an amine compound, in particular the amino acid glycine. The sodium sulfite and the amino acid react with glutaraldehyde to form a yellow-colored complex.

In practice, the commercial product utilizing the principles described in U.S. Pat. Nos. 4,521,376 and 4,463,980 involves a three-step reaction. First, glutaraldehyde is reacted with sodium sulfite to form a sulfite addition product and sodium hydroxide. Second, sodium hydroxide reacts with glycine to form sodium glycinate. Third, sodium glycinate reacts with another molecule of glutaraldehyde to form a yellow-colored addition product. The test strips based on this chemical sequence are "semi-quantitative" chemical indicators for use in determining whether the concentration of glutaraldehyde is above or below an established minimum concentration for a solution. The test strips are commercially available as the CIDEX® family of solutions test strips (Johnson & Johnson Medical, Inc., Arlington, Tex., U.S.A.).

More precisely, the "semi-quantitative" test strip is a qualitative threshold test to determine whether the concentration of glutaraldehyde in a given sample meets a designated threshold. The test serves to indicate, either positively or negatively, whether the disinfectant solution contains a required minimum effective level of glutaraldehyde. A sample that contains the threshold level changes the color of the strip to yellow, indicating that the sample passes the assay. If the sample does not contain the threshold level of glutaraldehyde, the strip does not change to a yellow color, indicating that the sample fails the assay. The test does not provide a continuous quantitative assay of glutaraldehyde levels in the solution.

Likewise, other commercially available test strips also are qualitative, rather than quantitative, indicators of whether the aldehyde concentration in the disinfecting solution is above a threshold level. For example, a commercially available test strip for formaldehyde allows for assay of formaldehyde levels between 2.5% and 4.0% in the disinfecting solution. The qualitative commercial test strips contain the hydrochloride salt of glycine, which releases hydrochloric acid as a product of the reaction with formaldehyde. The release of hydrochloric acid in solution causes a color change in a pH indicator. These marketed strips are available under the trade name SERIM™ Formaldehyde Test Strips (Serim Research Corporation, Elkhart, Ind., U.S.A.). Moreover, the test strips do not provide a quantitative measurement of formaldehyde levels in the solution.

Reagent test strips also have been employed in testing steam sterilized products. The detection of formaldehyde vapor in dry or mixed steam is described in U.S. Pat. No. 4,328,182. The strip disclosed in U.S. Pat. No. 4,328,182 is a neutral, absorbent filter paper impregnated with an amino acid and a pH indicator. The strip is coated with a hydrophobic coating to control uptake of formaldehyde vapor in order to detect high range formaldehyde concentration. The strip is not used for quantitative testing. There is no appreciation that a reagent test strip can be used for measuring the concentration of a gaseous aldehyde other than formaldehyde, for example glutaraldehyde. Moreover, there is no mention or recognition that an amino acid, or a mixture thereof, can be used in combination with a protein to prepare quantitative dry reagent test strips for assay of aldehydes in general, either in an aqueous solution or as a gaseous vapor.

To date, no known single assay is available to quantitatively assay aldehyde concentrations because the nonlinear relationship between the degree of pH change and aldehyde concentration is not yet sufficiently defined to provide a differentiable pH range relative to the aldehyde concentration in a sample. The present invention does not attempt to define the relationship between the concentration of the aldehyde in an aqueous solution and the pH of the same. The present invention is directed to providing an assay for measuring an aldehyde concentration over the range of 0% to about 4%, and especially about 0.5% to about 4%, by weight, without requiring titration or inefficient sample handling.

The present invention, therefore, is directed to an assay method and device that can be used to assay a test sample containing 0% to 4%, by weight, or more, of an aldehyde. As illustrated hereafter, the present test strips have an accurate and wide detection range with a continuous color response from 0.5% to over 4%, by weight, aldehyde.

The present method of assaying for aldehyde content in a test sample yields trustworthy and reproducible results by utilizing an indicator reagent composition that undergoes a color transition in response to aldehyde concentration. Additionally, the method and composition utilized in the aldehyde assay does not adversely affect or interfere with any other test reagent pads that are present on a multiple test pad strip.

In accordance with the present invention, an indicator reagent composition can be incorporated into a carrier matrix to provide sufficient sensitivity and color differentiation to assay for aldehyde concentration over the range of 0% to greater than about 4%, and particularly about 0.5% to greater than about 4%, by weight, without requiring titration or inefficient sample handling. In addition, although dry phase test strips have been used to assay for aldehyde content, no dry phase test strip has been used to quantitatively assay an aqueous sample for aldehyde concentration.

SUMMARY OF THE INVENTION

The present invention is directed to a new and improved composition, device, and method of determining the aldehyde concentration in a test sample. A device includes a test pad comprising a suitable carrier matrix incorporating an indicator reagent composition capable of interacting with an aldehyde to produce a detectable response to aldehyde concentration. A carrier matrix of the test pad comprises a bibulous material, such as filter paper; a nonbibulous material, such as a strip, layer, or membrane of a polymerized material; or a mixture thereof. An indicator reagent composition is homogenously incorporated into the carrier matrix, and the carrier matrix holds the indicator reagent composition homogeneously throughout the carrier matrix while maintaining the permeability of the carrier matrix to the sample.

More particularly, the present invention is directed to a method of assaying the aldehyde content of an aqueous sample by utilizing a new indicator reagent composition. It has been demonstrated that a reagent composition including: (a) a protein, (b) an amine, (c) a color indicator, (d) an optional polymer, and (e) a carrier, for example water, affords excellent sensitivity to quantitatively assay a test sample for aldehyde content. The assay provides a method of determining the concentration of the aldehyde with sufficient color differentiation to quantitatively measure aldehyde concentration in the range of 0% to greater than 4% aldehyde, and particularly about 0.5% to greater than 4%, by weight, of the aldehyde, particularly aliphatic monoaldehyde and dialdehydes. The invention most preferably is used to detect levels of glutaraldehyde and formaldehyde concentrations.

An important feature of the present invention to provide an accurate and reliable quantitative determination for the concentration of an aldehyde in a liquid, typically aqueous, or gaseous sample. The quantitative determination can be achieved in accordance with the invention by allowing a test sample containing a concentration of aldehyde to interact with the indicator reagent composition. The indicator reagent composition responds to the aldehyde content of the sample, even at a high concentration, to provide a differentiable color transition. Quantitative assay of the test samples is more sensitive and more accurate than achieved with previously disclosed compositions in that the indicator reagent composition is able to detect and differentiate between high levels of aldehyde present in the sample without titration or multistep sample handling.

Therefore, one aspect of the invention provides a method and composition for quantitatively determining the concentration of aqueous or gaseous aldehyde. The composition interacts with the aldehyde to produce a change in color of a device that is indicative of the concentration of the aldehyde in the sample.

Another aspect of the invention is to provide a method of assaying a test sample containing aldehyde, said method having sufficient sensitivity and visual color resolution to allow differentiation between, and quantitative measurement of, samples having different concentrations of aldehydes, including glutaraldehyde and formaldehyde in particular.

Yet another aspect of the invention is to provide a sensitive method of assaying samples for aldehyde concentration over the range of 0% to greater than about 4% by weight aldehyde. The present method is especially useful in the detection of a high concentration of aldehyde, i.e., about 0.5% to greater than about 4% by weight of the sample.

Another aspect of the present invention is to provide an indicator reagent composition that interacts with an aldehyde, and undergoes a visually or instrumentally differentiable color transition to allow determination of the aldehyde concentration in the sample.

Another aspect of the present invention is to provide a method of assaying the aldehyde content of a sample by incorporating an indicator reagent composition into a dry phase detection device, wherein the indicator reagent composition comprises: (a) a protein, (b) an amine, (c) a color indicator, (d) an optional polymer, preferably a cellulose-based polymer, and (e) a carrier, such as water.

Still another aspect of the present invention is to provide a new and improved method of determining the aldehyde content of an aqueous sample by utilizing a test device, including a carrier matrix, said carrier matrix comprising a bibulous matrix, like filter paper, or a nonbibulous matrix, like a glass fiber or a layer of a permeable polymeric material, and said carrier matrix having incorporated therein an indicator reagent composition capable of interacting with an aldehyde present in the sample, to provide a color transition that can be correlated to the concentration of the aldehyde in the sample.

A further aspect of the present invention is to provide an improved dry phase test strip that incorporates an indicator reagent composition comprising (a) a protein, (b) an amine, (c) a color indicator, and (d) an optional polymer, and thereby provide a quantitative assay for the aldehyde content in a sample.

The above and other aspects, advantages, and novel features of the present invention will become apparent from the following detailed description of the invention.

DETAILED DESCRIPTION OF THE PREFERRED EMBODIMENTS

In accordance with the method of the present invention, a quantitative assay of aqueous samples for aldehyde content, and especially high concentrations of an aldehyde, is accomplished by utilizing an indicator reagent composition that includes (a) a protein, (b) an amine, (c) a color indicator, (d) an optional polymer, and (e) a carrier. By employing an indicator reagent composition of the present invention, sufficient sensitivity and sufficient visual color differentiation between samples of different aldehyde content is achieved. In accordance with the method of the present invention, samples having an aldehyde content of 0% to greater than about 4%, and particularly about 0.5% to greater than about 4%, by weight of the sample, can be measured and differentiated.

To achieve the full advantage of the present invention, the method and composition are employed in dry phase, test pad assays to determine the concentration of an aldehyde in an aqueous solution or, alternatively, a gaseous vapor. The aldehyde commonly is a component of a germicide solution, for example glutaraldehyde or formaldehyde. A dry phase test strip, including a test pad comprising a carrier matrix incorporating an indicator reagent composition of the present invention, allows the rapid quantitative assay of samples by visual means.

In particular, the present invention allows determination of aldehyde concentration of the sample by the visual color change of a test pad on a test strip resulting from contact between the test strip and the sample. The aldehyde concentration of the sample is determined by correlating the detected color change to the aldehyde concentration of the sample. The test strip includes a test pad comprising an inert carrier matrix incorporating an indicator reagent composition. The present method allows rapid calorimetric determination of the aldehyde concentration of a sample, especially providing a suitable method for quantitatively measuring the concentration of the aldehyde in aqueous solution.

Previous assay methods employed compositions that were unable to distinguish between aqueous solutions containing different concentrations of aldehyde above about 1.5%, by weight. The prior compositions utilized end point indicators without proteins, making discrimination between different pH levels induced by different concentrations of the aldehyde indistinguishable. In contrast, the present method detects the content of aldehyde in the sample by utilizing an indicator reagent composition containing a protein that improves the overall quantifiable range of the aldehyde.

Accordingly, one component of the present indicator reagent composition is the protein. Examples of suitable proteins are serum albumins, such as human serum albumin, bovine serum albumin, and ovalbumin; serum globulins, for example, gamma globulin; and the like. The proteins are protein fractions of blood serum which, when added to the indicator reagent composition, can improve the quantifiable range for detecting aldehyde concentration. Typically, the protein is present in the indicator reagent composition in an amount of about 1% to about 25%, and preferably about 3% to about 20%, by weight of the indicator reagent composition. To achieve the full advantage of the present invention, the indicator reagent composition contains about 3% to about 15% by weight of a protein.

The protein component is used in combination with an amine component of the indicator reagent composition to achieve a quantitative assay for the concentration for an aldehyde by correlating the change in pH with a color indicator. The amine component is present in the indicator reagent composition in an amount of about 5% to about 25%, and preferably about 10% to about 20%, by weight.

The amine compound typically is an amino acid, and more particularly a lower amino acid having a slightly acidic to neutral pH when dissociated in water. In preferred embodiments, the amine compound is an amino acid or peptide comprising at least two amino acids represented by the general formula:

wherein R is hydrogen or alkyl optionally substituted with amino, guanidino, carboxy, hydroxy, ureido, or sulfhydryl. Preferably, the alkyl group is a straight chain alkyl group containing from about one to four carbon atoms.

As used herein, the term "alkyl" refers to a straight- or branched-chain hydrocarbon group, preferably containing about one to four carbon atoms, unless otherwise noted, which can be optionally substituted with one or more functional groups.

The term "amino" refers to a —$NH_2$ group.
The term "guanidino" refers to a —$NH(C=NH)NH_2$ group.
The term "carboxy" refers to a —COOH group.
The term "sulfhydryl" refers to a —SH group.
The term "hydroxy" refers to a —OH group.
Nonlimiting examples of amino acids suitable for the invention are alanine, arginine, asparagine, aspartic acid, cysteine, glycine, glutarmic acid, lysine, serine, threonine, ornithine, citrulline, and mixtures thereof. The preferred amino acids are lower amino acids, such as alanine, asparagine, and glycine. The amino acids commonly exist as a weak acid and have a slightly acidic to a slightly basic when dissolved in water, about pH 5 to about pH 7.

The amine also can be a peptide. Peptides suitable for the invention comprise two to about 5 amino acids having a formula (I), as described above. A preferred peptide is glycylglycine.

The amino acids and peptides can react with aldehydes, particularly aliphatic monoaldehyde and dialdehydes, to lower the pH of an aqueous solution. The term "aliphatic monoaldehyde or dialdehyde" refers to straight-chain hydrocarbon groups containing an aldehyde (—CHO) group, preferably containing from one to ten carbon atoms. More particularly, the term "monoaldehyde" refers to hydrocarbon groups containing one —CHO group. Like-wise, the term "dialdehyde" refers to hydrocarbon groups containing two —CHO groups.

To illustrate properties of the amino acids, aqueous solutions of amino acids, 10% by weight, were adjusted to a pH of 8.0 with sodium hydroxide. The change in pH of the solution was measured as formaldehyde and glutaraldehyde were added to the solution. The formaldehyde was added until about a 4%, by weight, solution was obtained. Glutaraldehyde was added until about a 2.5%, by weight, solution of glutaraldehyde was prepared. The pH shift of amino acid test solutions are summarized below.

| Amino Acid | Formaldehyde (4% by weight) | Glutaraldehyde (2.5% by weight) |
| --- | --- | --- |
| Alanine | 2.5 | 2.4 |
| Glycine | 3.8 | 3.8 |
| Glycylglycine | 3.8 | 1.2 |
| Aspartic Acid | 2.4 | 2.3 |
| Glutarmic Acid | 1.9 | 2.1 |
| Lysine | 3.6 | 0.4 |
| Arginine | 2.4 | 0.5 |
| Serine | 2.5 | 2.1 |
| Threonine | 2.8 | 2.5 |
| Cysteine | 3.9 | 1.6 |

As demonstrated above, the pH of each solution drops in response to an increase in the aldehyde in the presence of an amino acid. However, in the absence of a protein, the change in pH in the presence of the amino acid varies sharply and is difficult to modulate. The addition of buffers, for example inorganic phosphate and borate buffers, can improve the quantifiable range of the aldehyde concentration. Organic buffers, such as tris(hydroxymethyl) aminomethane, also can be used to modulate the pH change. Both inorganic and organic buffers, however, have little effect on the overall spread of the quantifiable range.

The invention, therefore, comprises a combination of a protein and an amine in the indicator reagent composition. Without being limited to any theory, it is theorized that the amine group forms a neutral carbamino adduct with the aldehyde. The formation of the carbamino adduct releases a carboxylic acid from the amine as a free acid. The protein serves as a competitive substrate for the aldehyde or forms a gel-like barrier to prevent overreaction of the amine substrate with the aldehyde. Incorporating the protein into the indicator reagent composition allows for the quantification of the directly proportional relationship between the amount of aldehyde and the change in pH induced by the release of the carboxylic acid from the amino acid.

Accordingly, it is possible to accurately quantify levels of aldehyde in the percent range using a dry reagent test strip instead of the parts per million range typically determined by titration. More particularly, glutaraldehyde concentrations of about 0.5, 1.0, 1.5, and 2.0% can be measured and differentiated. Formaldehyde concentrations of about 1, 2, 3 and 4% also can be measured and differentiated by the present invention.

As such, any protein that can function as a competitive substrate with the aldehyde or that can protect the reaction of the amine substrate from high levels of aldehyde content is suitable for the invention. By increasing or decreasing the concentration of the amino acid or peptide, the amine functionality of the amino acid or peptide can buffer the reagent system to achieve a desired gradient of pH changes. The use of the amino acid as the buffer has the added advantage in that, because the amino acid is both a substrate and a buffer, high amino acid concentrations will not diminish the sensitivity of the reagent system by reducing or narrowing the dynamic range of pH changes. Moreover, use of a single amino acid in the reagent composition eliminates unnecessary components and potential variables in manufacturing.

In addition to the protein component and the amine component, the indicator reagent composition contains a color indicator for distinguishing the change in pH. The pH of the solution decreases in a manner that can be quantitatively monitored by use of the color indicator. Preferably, the indicator is impregnated on a suitable carrier medium as part of the indicator reagent composition as described herein.

The color indicators suitable for the invention typically are pH indicators capable of undergoing a color change between about pH 3 and about pH 12. Examples of pH indicators suitable for the invention include, but are not limited to, bromphenol blue, tetrabromophenol blue, Congo red, methyl orange, bromchlorphenol blue, p-ethoxychrysoidine, alpha-naphthyl red, sodium alizarin-sulfonate, bromcresol green, 2,5-dinitrophenol, methyl red, lacmoid, litmus, chlorphenol red, benzoyl auramine G, azolitmin, bromcresol purple, bromphenol red, dibromophenol-tetrabromophenol-sulfonphthalein, p-nitrophenol, bromothymol blue, phenol red, neutral red, rosolic acid aurin, quinoline blue, cresol red, alpha-naphtholphthalein, metacresol purple, ethyl bis [2,4-dinitrophenyl]-acetate, tropaeolin, thymol blue, o-cresolphthalein, phenolphthalein, thymolphthalein, Nile blue A, alpha-naphtholbenzein, alizarin yellow GG, alizarin yellow R, and the like, or mixtures thereof. The preferred indicators for the invention are methyl orange, bromcresol green, bromphenol red, methyl red, bromothymol blue, neutral red, cresol red, metacresol purple (alkaline range), thymol blue (alkaline range), thymolphthalein, and other indicators which typically undergo color change between from about pH 3 and about pH 10.5. More particularly the preferred indicator is methyl red, which which indicates change in pH between from about pH 4.4 to about pH 6.2.

In accordance with the present invention, for example, the methyl red indicator is yellow at the high range of the pH concentration. A yellow color exhibited by the composition corresponds to the low range of the aldehyde concentration in the sample, about 0.5% and 1% of glutaraldehyde and formaldehyde, respectively. Conversely, at the low range of the pH concentration, the indicator is a pumpkin color or rose red color. Such colors correspond to the high range of the aldehyde concentration, about 2% and about 4% of glutaraldehyde and formaldehyde, respectively.

The indicator reagent composition also can optionally contain a polymer. Preferably, the polymer is a neutral, nonionic polymer. The indicator reagent composition can contain a mixture of polymers to achieve a broad range quantitative assay, and particularly a high range quantitative assay, for aldehyde content. The preferred polymers are water-soluble, cellulose-based polymers. Other water-soluble polymers, such as polyvinylpyrrolidone, also can be used as the polymer in the present indicator reagent composition.

The water-soluble, cellulose-based polymers are derivatives of cellulose wherein hydroxy groups on the sugar moiety of cellulose are modified with a short chain alkyl (i.e., $C_1$-$C_4$), alkyl alcohol, or alkyl carboxylic acid. Examples of some common cellulose modifications are replacing a portion of the hydroxy groups with methyl, hydroxymethyl, hydroxyethyl, hydroxyethylmethyl, hydroxypropyl, hydroxypropylmethyl, or carboxymethyl groups, for example.

Examples of water-soluble cellulose-based polymers useful in the present invention include, but are not limited to, methylcellulose, hydroxymethylcellulose, hydroxyethylcellulose, hydroxyethylmethylcellulose, hydroxypropylcellulose, hydroxypropylmethylcellulose, carboxymethylcellulose and salts thereof, hydroxybutylcellulose, cellulose acetate, carboxymethylhydroxyethylcellulose, hydroxybutylmethylcellulose, and mixtures thereof.

In addition to cellulose-based polymers, other water-soluble polymers can be used in the method and composition of the present invention. Such water-soluble polymers are neutral, nonionic polymers, for example, polyvinylpyrrolidone, hydrolyzed polyvinylpyrrolidone, poly(vinyl alcohol), poly(vinyl acetate), vinyl acetate-vinyl alcohol copolymers, poly(methacrylamide), polyoxypropylene-polyoxyethylene block polymers having one of the following structures:

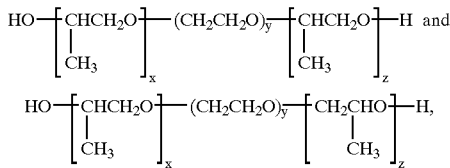

wherein x and z, independently, are an integer from about 4 to about 30, and y is an integer from about 4 to about 100, polyacrylamide, vinyl alcohol copolymers, and mixtures thereof.

The polymer is present in the indicator reagent composition in an amount of 0% to about 5%, and preferably about 0.2% to about 2%, by weight of the indicator reagent composition. To achieve the full advantage of the present invention, a water-soluble polymer is present in the indicator reagent composition in an amount of about 1% to about 2%, by weight of the composition.

The indicator reagent composition optionally can contain other chemically nonreactive ingredients. For example, one optional ingredient is a surfactant, in particular an anionic surfactant or a nonionic surfactant. The surfactant improves the ability of the sample to wet the carrier matrix, and the surfactant also improves the stability of the color transition of the indicator in response to the aldehyde.

The surfactant is present in the indicator reagent composition in an amount of 0% to about 1.5%, and preferably about 0% to about 1%, by weight of the composition. To achieve the full advantage of the present invention, the surfactant is present in an amount of about 0% to about 0.5% by weight of the composition.

Useful nonionic surfactants include, but are not limited to, an ethoxylated polysorbate, an ethoxylated alcohol, an ethoxylated phenol, i.e., an ethoxylated octylphenol, nonylphenol, or dodecylphenol with about 8 to about 30 moles of ethylene oxide, a polyethylene glycol, e.g., PEG-8 through PEG-40, a polypropylene glycol, e.g., PPG-9 through PPG-34, an ethylene glycol-propylene glycol copolymer, e.g., a poloxamer, and similar nonionic surfactants, and mixtures thereof. In general, a useful nonionic surfactant has an HLB value of about 6 to about 25.

Anionic surfactants useful in the present invention are not particularly limited. Usually, the anionic surfactant includes a hydrophobic moiety, such as a carbon chain including about eight carbon atoms to about 30 carbon atoms, and particularly about twelve carbon atoms to about twenty carbon atoms; and further includes a hydrophilic moiety, such as sulfate, sulfonate, carbonate, phosphate, or carboxylate. Often, the hydrophobic carbon chain is etherified, such as with ethylene oxide or propylene oxide, to impart a particular physical property or reduced surface tension, to the anionic surfactant.

The anionic surfactants are well known, and can be a fatty acid, a salt of a fatty acid, an ethoxylated fatty acid, or a salt of an ethoxylated fatty acid, for example. Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkyloxy alkane sulfonates, alkyl arylsulfonates, alkyl carbonates, alkyl ether carboxylates, fatty acids, sulfosuccinates, alkyl ether sulfosuccinates, sarcosinates, octoxynol phosphates, nonoxynol phosphates, taurates, fatty taurides, sulfated monoglycerides, fatty acid amido polyoxyethylene sulfates, and isothienates; or mixtures thereof. Many additional anionic surfactants are described in *McCutcheon's, Detergents and Emulsifiers*, 1993 *Annual*, published by McCutcheon Division, MC Publishing Co., and incorporated herein by reference.

The alkyl sulfates and alkyl ether sulfates are particularly effective classes of anionic surfactants. Examples of anionic surfactants useful in the composition and method of the present invention include, but are not limited to, the ammonium, monoethanolamine, diethanolamine, triethanolamine, isopropylamine, sodium, potassium, lithium, or magnesium salt of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or mixtures thereof. Examples of especially useful anionic surfactants are a lauryl sulfate salt, a lauryl ether sulfate salt, a lauryl phosphate salt, a sulfosuccinate salt, a dodecylsulfonate salt, a cholate salt, a $C_8$ to $C_{18}$ fatty acid, and mixtures thereof.

The carrier for the ingredients of an indicator reagent composition includes water. However, organic solvents, such as acetone, methanol, ethanol, isopropyl alcohol, ethylene glycol, propylene glycol, dimethylformamide, dimethylsulfoxide, acetonitrile, ethylacetate, and similar solvents, can be included in the carrier vehicle. The selection of a suitable organic solvent or solvents, in addition to water, to include in the carrier of the indicator reagent composition is within the capability of those skilled in the art of designing diagnostic assays.

The amount of organic solvent present in an indicator reagent composition generally is 0% to about 90%, and preferably about 10% to about 70%, by weight of the carrier. A carrier comprising water and an organic solvent, like methanol, ethanol, or acetone, is especially preferred because a carrier matrix impregnated with the indicator reagent composition can be dried within a few to several minutes.

The carrier matrix of the invention can be any substance capable of incorporating the chemical reagents required to perform the assay of interest, as long as the carrier matrix is substantially inert with respect to the chemical reagents. The carrier matrix also is porous or absorbent relative to the liquid sample.

The expression "carrier matrix" refers either to bibulous or nonbibulous matrices that are insoluble in the carrier of the indicator reagent composition and other physiological fluids and that maintain their structural integrity when exposed to the carrier and other physiological fluids. Suitable bibulous matrices include filter paper, sponge materials, cellulose, wood, woven and nonwoven fabrics, and the like. Nonbibulous matrices include glass fiber, polymeric films, and microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulose beads, and especially fiber-containing papers such as filter paper or chromatographic paper; synthetic or modified naturally occurring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. The carrier matrix can be of different chemical compositions or a mixture of chemical compositions. The matrix also can vary in regards to smoothness and roughness combined with hardness and softness. The handle usually is formed from hydrophobic materials such as cellulose acetate, polyethylene terephthalate, polycarbonate, or polystyrene. The carrier matrix is most advantageously constructed from filter paper or polymeric films.

The carrier matrix of the test strip can be any bibulous or nonbibulous material that allows permeation by the sample to saturate the test pad of the test strip that is impregnated with the indicator reagent composition. A preferred carrier matrix is a hydrophilic, bibulous matrix, including cellulosic materials, such as paper, and preferably filter paper. The carrier matrix also can be a hydrophilic, nonbibulous matrix, including polymeric films, such as a polyurethane or a crosslinked gelatin. Such polymeric films possess all of the qualities required of a carrier matrix of the present invention, including suspending and positioning both the essential ingredients and any optional ingredients included in the indicator reagent composition, and permeability of the sample through the carrier matrix.

The present invention can be used to assay an undiluted sample for aldehyde concentration. As previously described, certain aldehydes, for example glutaraldehyde and formaldehyde, are commonly used to disinfect medical equipment, more particularly hemodialyzers. Most indicator reagent compositions cannot quantitatively assay undiluted samples for a high concentration of aldehyde because the pH spread cannot be differentiated and quantified.

Moreover, dry reagent test strips that are currently available on the commercial market detect only the presence of the disinfecting agent, i.e., either glutaraldehyde and formaldehyde, relative to an established threshold level. The commercially available dry reagent test strips cannot quantitatively determine the amount of aldehyde present in a sample.

In contrast, the present invention can be used to assay undiluted samples for aldehyde concentration over the range of 0% to greater than about 4%, and especially about 0.5% to greater than about 4%, by weight, of the composition. This capability greatly increases versatility of the invention because medical workers often use aldehyde-containing germicide solutions to sanitize hemodialyzer units. The effectiveness of the germicide solutions is directly dependent on the concentration of aldehyde in the sample. The composition of the invention, therefore, can be used by medical personnel as a test for quantitatively identifying the amount of aldehyde in a sample either as an aqueous solution or as a gaseous vapor. In particular, the change in pH of an aqueous solution can be measured by incorporating the composition into a dry reagent test strip or by using the composition as an indicator solution.

The indicator reagent composition undergoes a color transition upon contact with the sample to provide an assay for aldehyde concentration from the intensity and degree of the color transition. The indicator reagent composition of the present invention provides a sufficiently resolved and differentiated color transition such that the aldehyde content in the sample can be measured and accurately determined without the use of color-measuring instruments, such as spectrophotometers or calorimeters, over a concentration range of 0% to greater than about 4%, by weight of the composition. However, if desired, such color-measuring instruments can be used to measure the difference in color degree and intensity between the sample and a solution having a known concentration of aldehyde.

The intensity and degree of the color transition are used to determine the aldehyde content of the sample by comparing or correlating the color produced by the sample to colors produced by solutions having a known aldehyde concentration. In accordance with an important feature of the present invention, the indicator reagent composition provides a sufficiently resolved and differentiated color transition such that the aldehyde content of an undiluted sample can be measured for an aldehyde content of 0% to greater than about 4% by weight without the use of color-measuring instruments.

An indicator reagent composition of the present invention, as described above, can be used in dry phase, test pad assays for aldehyde. The dry phase, test pad assay for aldehyde utilizing a present indicator reagent composition is performed in accordance with methods well known in the art. In general, the assay for aldehyde is performed by contacting the sample with an indicator reagent composition, which typically is incorporated into an analyte detection device. In one method, the analyte detection device is contacted with an aqueous sample by dipping the analyte detection device into the aqueous sample. Alternatively, the aqueous sample can be applied to the analyte detection device dropwise. The resulting change in color of the analyte detection device reveals the aldehyde concentration of the sample; and, if so designed, the resulting color transition can be compared to a standardized color chart to provide a measurement of the aldehyde concentration of the sample.

The amount of aldehyde also can be detected in a gaseous vapor, for example as a component of sterilizing steam treatment or as a vapor mix, such as a formaldehyde vapor mix. To measure the aldehyde content of the gaseous sample, the analyte detection device is directly exposed to the gaseous medium containing the aldehyde by, for example, suspending the device in the medium.

Typically, the analyte detection device is a test strip impregnated with an indicator reagent composition, designed either as a single pad test strip (to assay only for a single analyte) or as a multiple pad test strip (to assay for several analytes simultaneously). For either type of test strip, the test strip includes a support strip, or handle, normally constructed from a hydrophobic plastic, and a reagent test pad, comprising a bibulous or nonbibulous carrier matrix. In general, the carrier matrix is an absorbent material that allows the liquid sample to move in response to capillary forces through the matrix to contact the indicator reagent composition and produce a detectable and measurable color transition.

In accordance with the method of the present invention, to perform a dry phase test strip assay for aldehyde, an aqueous solution, including: (a) about 3% to about 25%, by weight, of a protein; (b) about 5% to about 25% by weight of an amine; (c) about 0.05% to about 0.15% by weight of a color indicator; (d) about 0.2% to about 5% by weight of a polymer, like a cellulose-based polymer; and (e) any other desired optional ingredients, or solvents, first is prepared. A nonbibulous matrix, such as a polyurethane film, or a bibulous matrix, such as filter paper, then is saturated or impregnated with the aqueous solution by immersing or by spraying the aqueous solution onto sheets or precut strips or pads of the polyurethane film or filter paper.

Then, after removing the aqueous solvent by drying in a forced air oven at a temperature of about 40° C. to about 100° C. for about 2 to about 15 minutes, the impregnated polyurethane film or filter paper, if necessary, is cut to an appropriate size, such as a pad having dimensions from about 0.2 in. (inch) (0.5 cm) by about 0.5 in (1.3 cm) to about 0.5 in. (1.3 cm) by about 1 in. (2.5 cm).

It should be understood that it is well within the experimental techniques of those skilled in the art of preparing test devices to determine the proper balance between size of the test pad, the strength of indicator reagent composition solutions, the amount of sample, and the method of introducing the sample to the test strip, such as by pipetting rather than dipping, in order to design a quantitative assay for aldehyde content utilizing the method and composition of the present invention.

The dried, impregnated polyurethane film or filter paper then is secured to an opaque or transparent hydrophobic plastic handle with double-sided adhesive tape. The resulting test strip then is contacted with a sample for a sufficient time to saturate the test pad with the sample. After waiting a predetermined time, such as from about 1 to about 120 seconds, the test strip is examined, either visually or by instrument, for a response. The color transition, if any, of the test pad reveals the concentration of aldehyde in the sample.

In many cases, simple visual observation of the test strip provides the desired information. If more accurate information is required, a color chart bearing color spots corresponding to various known concentrations of aldehyde can be prepared for the particular indicator reagent composition used in the test strip. The resulting color of the test strip after contact with the sample then can be compared with the color spots on the chart to determine the concentration of aldehyde in the sample. If a more accurate determination is required, a spectrophotometer or calorimeter can be used to more precisely determine the degree of the color transition. In addition, the dry phase test strip assay can be made quantitative by employing spectrophotometric or calorimetric techniques, as opposed to visual techniques, in order to more reliably and more accurately measure the degree of color transition, and, therefore, more accurately measure the concentration of aldehyde in the sample.

In accordance with one embodiment of the present invention, the following dry phase test strips were prepared for a two-fold purpose: (1) to perform a dry phase assay for aldehyde (Strip B only) and (2) to compare the indicator reagent composition without protein versus with protein. All amino acids, buffers, proteins, and pH indicators were purchased from Sigma-Aldrich (St. Louis, Mo., U.S.A.). Cellulose-based polymers were purchased from Aqualon Company (Wilmington, Del., U.S.A.).

EXAMPLE I

Solutions having the following components were prepared in water and adjusted to pH 7.9 with sodium hydroxide. Filter paper, such as Schleicher & Schull #903 absorption paper, was immersed in a solution to impregnate solution components onto the paper. Excess solution was removed from the surface of the filter paper with a scraper bar.

| | INDICATOR REAGENT COMPOSITION Amount of Ingredient (Weight % of solution) | |
|---|---|---|
| Ingredient | Strip A (comparative) | Strip B |
| Bovine Serum Albumin | — | 5% |
| Glycine | 20% | 20% |
| Methyl Red | 0.01% | 0.01% |
| Hydroxyethylcellulose | 0.2% | 0.2% |

The filter paper was dried at 65° C. for 10 to 20 minutes in a forced-air oven. The dried impregnated filter paper was backed with double-sided adhesive, and slit into 0.2 inch (0.5 cm) wide ribbons. A ribbon of filter paper incorporating the indicator reagent composition of the present invention then was attached to a polystyrene plastic support (10 mil) by means of the double-sided adhesive. The plastic support, including the saturated or impregnated filter paper, was slit into 0.2 inch (0.5 cm) wide strips. Accordingly, the plastic support included a pad having dimensions of saturated or impregnated filter paper to provide a test pad comprising a filter paper carrier matrix incorporating an indicator reagent composition of the present invention.

A stock solution of 37% formaldehyde was diluted with deionized water to concentrations of 1, 2, 3 and 4% to obtain a series of test solutions. The prepared strips were dipped into the series of test solutions. The excess was removed by touching the side of the strip with a paper absorbent, for example a paper towel. The color of the treated portion of the test strip was recorded after 60 seconds. The color response of each impregnated strip is shown below in Table 1.

TABLE 1

Color response of dry reagent strips containing indicator reagent composition without protein versus with protein to increasing formaldehyde concentration

| | Color Response of Dry Reagent Strip | |
|---|---|---|
| Formaldehyde Concentration | Strip A (comparative) | Strip B |
| 1% | Yellow | Yellow |
| 2% | Rose Red | Orange |
| 3% | Rose Red | Pumpkin |
| 4% | Rose Red | Rose Red |

Using similar procedures as the steps required to prepared the test formaldehyde procedures, a stock solution of 25% glutaraldehyde was diluted with deionized water to concen trations of 0.5, 1.0, 1.5 and 2.0% to give a series of test solutions. The test solutions were tested with the prepared strips and the results are reported below in Table 2.

TABLE 2

Color response of dry reagent strips containing indicator reagent composition without protein versus with protein to increasing glutaraldehyde concentration

| | Color Response of Dry Reagent Strip | |
|---|---|---|
| Glutaraldehyde Concentration | Strip A (comparative) | Strip B |
| 0.5% | Orange | Yellow |
| 1.0% | Rose Red | Lemon |
| 1.5% | Rose Red | Orange |
| 2.0% | Rose Red | Pumpkin |

In particular, the data in Tables 1 and 2 demonstrate that the presence of the protein, bovine serum albumin, in the indicator reagent composition greatly improves the overall quantitation range of the aldehyde. This principle is evidenced by the comparison between comparative dry reagent Strip A, containing no protein, and the dry reagent Strip B, containing 5% protein in the reagent indicator composition. The strip containing the protein exhibits a unique color at each quantitation level, whereas the strip without protein detected only a differentiation at the 0.5% and 1.0% levels of glutaraldehyde concentration, and the 1% and 2% levels of formaldehyde concentration. The increased ability to differentiate a particular pH over the pH range is an important advantage for identifying and quantifying aldehyde content in a sample, and is quite unexpected in light of the present state of the art.

EXAMPLE II

The procedure for preparing the solution of Strip B above, as described in Example I, was repeated except substituting 5% by weight protein, bovine serum albumin, for the following concentrations of the desired proteins. For the preparation of Strip C, 3.5% by weight human serum albumin was substituted for the 5% by weight bovine serum albumin. For the preparation of Strip D, 20% by weight ovalbumin was substituted for the 5% by weight bovine serum albumin. For the preparation of Strip E, 20% by weight gamma globulin was substituted for the 5% by weight bovine serum albumin. Each solution was used to prepare impregnated strips in a manner in accordance with Example I, except substituting the solutions for Strip C, Strip D and Strip E for the solution used to prepare Strip B. The concentrations of protein in the solutions for the preparation of each strip are summarized below.

| | Strip C | Strip D | Strip E |
|---|---|---|---|
| Protein Concentration | 3.8% Human Serum Albumin | 20% Ovalbumin | 20% Gamma Globulin |

The color response of the impregnated strips was tested according to the procedures described above in Example I for the assay of the formaldehyde test solutions. The results are reported below in Table 3.

TABLE 3

Color response of indicator reagent composition to increasing formaldehyde concentration

| Formaldehyde | Color Response of Dry Reagent Strip | | |
|---|---|---|---|
| Concentration | Strip C | Strip D | Strip E |
| 1% | Orange | Orange | Tangerine |
| 2% | Tangerine | Tangerine | Pumpkin |
| 3% | Pumpkin | Pumpkin | Rose Red |
| 4% | Rose Red | Rose Red | Rose Red |

The impregnated strips were additionally tested according to the procedures described above in Example I for the assay of the glutaraldehyde test solutions. The results are reported below in Table 4.

TABLE 4

Color response of indicator reagent composition to increasing glutaraldehyde concentration

| Glutaraldehyde | Color Response of Dry Reagent Strip | | |
|---|---|---|---|
| Concentration | Strip C | Strip D | Strip E |
| 0.5% | Yellow | Yellow | Lemon |
| 1.0% | Lemon | Lemon | Orange |
| 1.5% | Orange | Orange | Pumpkin |
| 2.0% | Pumpkin | Pumpkin | Pumpkin |

The results summarized in Tables 3 and 4 show the effectiveness of proteins in addition to bovine serum albumin when incorporated in a composition of the invention. As shown above in Tables 3 and 4, human serum albumin, ovalbumin, and gamma globulin demonstrate an unique color response at all or nearly all levels of the quantitation ranges for glutaraldehyde and formaldehyde, respectively.

The results set forth in Tables 1, 2, 3 and 4 show that a test strip of the present invention is capable of assaying for aldehyde content over an entire range of 0% to greater than 4% by weight. More specifically, the data show that the invention can provide a quantitative determination for a formaldehyde concentration range of from about 1% to about 4% by weight of the total weight of the sample and for a glutaraldehyde concentration range from about 0.5% to about 2.0% by weight of the total weight of the sample.

From the visual assays and the data presented in Tables 1-4, it has been demonstrated that an indicator reagent composition of the present invention accurately assays for high levels of aldehyde, directly and quantitatively. In preferred embodiments, the composition contains a mixture of lower amino acids with a protein, each combination having a different response intensity and response range to the aldehyde levels. If desired, the composition can be adjusted to detect and measure a specific concentration of aldehyde. The color differentiations between different concentrations of aldehyde are excellent, therefore, the composition can be used in a quantitative test, rather than qualitative, test.

In accordance with an important feature of the present invention, the continuing and substantial problems in dry phase test strips for quantitatively assaying a sample for high concentrations of aldehydes are essentially eliminated. An indicator reagent composition of the present invention provides a differentiable response to the aldehyde concentration over a range of 0% to greater than about 4%, and particularly about 0.5% to greater than about 4%, by weight of the sample. Therefore, accurate and reliable assays for aldehyde content in undiluted samples can be performed by utilizing an indicator reagent composition and device of the present invention.

Modifications and variations of the invention as hereinbefore set forth can be made without departing from the spirit and scope thereof, and, therefore, only such limitations should be imposed as are indicated by the appended claims.

What is claimed is:

1. A composition comprising:
   (a) about 1% to about 25%, by weight, of a protein;
   (b) about 5% to about 25%, by weight, of an amine;
   (c) a color indicator;
   (d) an optional polymer; and
   (e) a carrier comprising water, said composition capable of exhibiting a detectable and measurable color transition in response to a concentration of 0% to greater than 4%, by weight, of an aldehyde.

2. The composition of claim 1 wherein the protein comprises bovine serum albumin, human serum albumin, ovalbumin, gamma globulin, or a mixture thereof.

3. The composition of claim 1 wherein the amine is an amino acid or a peptide comprising at least two amino acids of the formula:

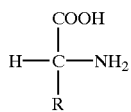

wherein R is hydrogen or alkyl, optionally substituted with amino, guanidino, carboxy, sulfhydryl, hydroxy, ureido, or hydroxy.

4. The composition of claim 3 wherein the amino acid comprises alanine, asparagine, glycine, lysine, arginine, aspartic acid, glutamic acid, cysteine, serine, ornithine, citrulline, or threonine.

5. The composition of claim 3 wherein the peptide comprises two to about five amino acids.

6. The composition of claim 3 wherein the peptide comprises glycylglycine.

7. The composition of claim 1 wherein the amine compound is present in an amount of about 10% to about 20%, by weight of the composition.

8. The composition of claim 1 wherein the optional polymer is a neutral, nonionic polymer.

9. The composition of claim 8 wherein the polymer comprises a water-soluble, cellulose-based polymer.

10. The composition of claim 8 wherein the cellulose-based polymer is selected from the group consisting of methylcellulose, hydroxymethylcellulose, hydroxyethylcellulose, hydroxyethylmethylcellulose, hydroxypropylcellulose, hydroxypropylmethylcellulose, carboxymethylcellulose and salts thereof, hydroxybutylcellulose, cellulose acetate, carboxymethylhydroxyethylcellulose, hydroxybutylmethylcellulose, and mixtures thereof.

11. The composition of claim 8 wherein the polymer comprises hydroxyethylcellulose.

12. The composition of claim 10 wherein the polymer comprises a water-soluble polymer selected from the group consisting of polyvinylpyrrolidone, hydrolyzed polyvinylpyrrolidone, poly(vinyl alcohol), poly(vinyl acetate), vinyl acetate-vinyl alcohol copolymer, poly (methacrylamide), a polyoxypropylene-polyoxyethylene block polymer having a structure:

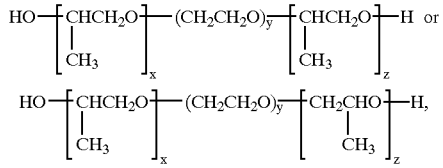

wherein x and z, independently, are an integer from about 4 to about 30, and y is an integer from about 4 to about 100, polyacrylamide, a vinyl alcohol copolymer, and mixtures thereof.

13. The composition of claim 1 wherein the polymer comprises an amount of 0% to about 5%, by weight of the composition.

14. The composition of claim 1 further comprising a nonionic or an anionic surfactant in an amount of 0% to about 1.5% by weight of the composition.

15. The composition of claim 14 wherein the surfactant is selected from the group consisting of an ethoxylated polysorbate, an ethoxylated alcohol, an ethoxylated phenol, a polyethylene glycol, a polypropylene glycol, an ethylene glycol-propylene glycol copolymer, an alkyl sulfate, an alkyl ether sulfate, an alkyl ether sulfonate, a sulfate ester of an alkylphenoxy polyoxyethylene ethanol, an alpha-olefin sulfonate, a beta-alkyloxy alkane sulfonate, an alkyl arylsulfonate, an alkyl carbonate, an alkyl ether carboxylate, a fatty acid, a sulfosuccinate, an alkyl ether sulfosuccinate, a sarcosinate, an octoxynol phosphate, a nonoxynol phosphate, a taurate, a fatty tauride, a sulfated monoglyceride, a fatty acid amido polyoxyethylene sulfate, and mixtures thereof.

16. The composition of claim 1 comprising:
   (a) about 1% to about 25% by weight protein;
   (b) about 5% to about 25% by weight amino acid or peptide;
   (c) about 0.005% to about 0.015% by weight color indicator;
   (d) about 0.2% to about 5% by weight of hydroxypropylcellulose, hydroxyethylcellulose, methylcellulose, hydroxymethylcellulose, carboxymethylcellulose, polyvinylpyrrolidone, and mixtures thereof.

17. The composition of claim 1 wherein the carrier further comprises an organic solvent.

18. The composition of claim 19 wherein the organic solvent comprises methanol, ethanol, or acetone.

19. The composition of claim 1 wherein the composition has a pH of from about 5 to about 11.

20. The composition of claim 1 wherein the color indicator changes color in the range from about pH 3 to about pH 12.

21. The composition of claim 1 wherein the color indicator is selected from the group consisting of bromphenol blue, tetrabromophenol blue, Congo red, methyl orange, bromchlorphenol blue, p-ethoxychrysoidine, alpha-naphthyl red, sodium alizarinsulfonate, bromcresol green, 2,5-dinitrophenol, methyl red, lacmoid, litmus, chlorphenol red, benzoyl auramine G, azolitmin, bromcresol purple, bromphenol red, dibromophenol-tetra-bromophenol-sulfonphthalein, p-nitrophenol, bromothymol blue, phenol red, neutral red, rosolic acid aurin, quinoline blue, cresol red, alpha-naphtholphthalein, metacresol purple, ethyl bis[2,4- dinitrophenyl]acetate, tropaeolin, thymol blue, o-cresolphthalein, phenolphthalein, thymolphthalein, Nile blue A, alpha-naphtholbenzein, alizarin yellow GG, alizarin yellow R, and mixtures thereof.

22. A method of determining aldehyde content of a sample containing 0% to greater than 4% by weight aldehyde, said method comprising:
   (a) contacting the sample with an indicator reagent composition comprising:
      (i) about 1% to about 25%, by weight, of a protein,
      (ii) about 5% to about 25%, by weight, of an amine,
      (iii) a color indicator, and
      (iv) an optional polymer; and
   (b) determining the aldehyde content of the sample from the intensity and degree of a color transition of the indicator reagent composition.

23. The method of claim 20 wherein the sample has an aldehyde content of 0.5% to greater than 4% by weight aldehyde.

24. The method of claim 22 wherein the aldehyde is glutaraldehyde or formaldehyde.

25. The method of claim 22 wherein the intensity and degree of the color transition are determined visually or instrumentally.

26. The method of claim 22 wherein the amine is an amino acid or a peptide.

27. The method of claim 22 wherein the sample is an aqueous sample or a gaseous sample.

28. A method of quantitatively determining the aldehyde content of a sample containing 0% to greater than 4% by weight aldehyde, said method comprising:
   (a) contacting the sample with an analyte detection device comprising a test pad, said test pad having incorporated therein an indicator reagent composition comprising a carrier matrix impregnated with a solution comprising:
      (i) about 1% to about 25%, by weight, of a protein,
      (ii) about 5% to about 25%, by weight, of an amine,
      (iii) a color indicator, and
      (iv) an optional polymer; and
   (b) determining the aldehyde content of the aqueous sample from the intensity and degree of a color transition of the indicator reagent composition.

29. The method of claim 28 wherein the aldehyde is glutaraldehyde or formaldehyde.

30. The method of claim 28 wherein the aldehyde is present in an aqueous solution or in a gaseous vapor.

31. The method of claim 28 wherein the amine is an amino acid or peptide.

32. A method of determining the aldehyde content of an aqueous sample comprising:
   (a) contacting the aqueous sample with an analyte detection device comprising a test pad having incorporated therein a solution comprising:
      (i) about 1% to about 25%, by weight, of a protein,
      (ii) about 5% to about 25%, by weight, of an amine,
      (iii) a color indicator,
   (b) examining the analyte detection device for a color transition; and
   (c) correlating the color transition to the aldehyde content of the aqueous sample.

33. The method of claim 32 wherein the aqueous sample has an aldehyde content of 0% to about 4% by weight.

34. The method of claim 32 wherein the aldehyde is glutaraldehyde or formaldehyde.

35. The method of claim 32 wherein the amine is an amino acid or peptide.

36. An analyte-detection device to determine the aldehyde content of an aqueous sample comprising:
   a support strip;
   a test pad; and
   an indicator reagent composition incorporated into the test pad, said reagent composition comprising:
      (a) about 1% to about 25%, by weight, of a protein,
      (b) about 5% to about 25%, by weight, of an amine,
      (c) a color indicator, and
      (d) an optional polymer.

* * * * *